United States Patent
Yang et al.

(10) Patent No.: US 8,546,091 B2
(45) Date of Patent: Oct. 1, 2013

(54) AKT PHOSPHORYLATION AT SER473 AS AN INDICATOR FOR TAXANE-BASED CHEMOTHERAPY

(75) Inventors: Sherry X. Yang, Ellicott City, MD (US); Sandra M. Swain, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/322,140

(22) PCT Filed: May 21, 2010

(86) PCT No.: PCT/US2010/035816
§ 371 (c)(1),
(2), (4) Date: Feb. 3, 2012

(87) PCT Pub. No.: WO2010/135671
PCT Pub. Date: Nov. 25, 2010

(65) Prior Publication Data
US 2012/0142624 A1    Jun. 7, 2012

Related U.S. Application Data

(60) Provisional application No. 61/180,558, filed on May 22, 2009.

(51) Int. Cl.
*G01N 33/534* (2006.01)
*A61K 31/337* (2006.01)
*A61K 31/704* (2006.01)
*A61K 31/66* (2006.01)

(52) U.S. Cl.
USPC ............. 435/7.23; 514/449; 514/34; 514/110

(58) Field of Classification Search
USPC .......................... 435/7.23; 514/449, 34, 110
See application file for complete search history.

(56) References Cited

PUBLICATIONS

Andre, F. et al., "Expression patterns and predictive value of phosphorylated AKT in early-stage breast cancer", Annals of Oncology, 19(2):315-320, XP002599214.
Asakuma J. et al., "Selective Akt inactivation and tumor necrosis actor-related apoptosis-inducing ligand sensitization of renal cancer cells by low concentrations of paclitaxel" Cancer Res 2003;63(6):1365-70.
Bhaskar, P.T. et al. "The two TORCs and Akt" Dev Cell 2007;12(4):487-502.
De Laurentiis M. et al. "Taxane-based combinations as adjuvant chemotherapy of early breast cancer: a meta-analysis of randomized trials" J Clin Oncol 2008;26(1):44-53.
Early Breast Cancer Trialists' Collaborative Group (EBCTCG). "Effects of chemotherapy and hormonal therapy for early breast cancer on recurrence and 15-year survival: an overview of the randomised trials" Lancet 2005;365(9472):1687-717.

(Continued)

*Primary Examiner* — Rosanne Kosson
*Assistant Examiner* — Larry Moore
(74) *Attorney, Agent, or Firm* — Woodcock Washburn LLP

(57) ABSTRACT

Methods for determining whether a cancer patient is likely to benefit from treatment with a taxane compound based on Akt-Ser473 phosphorylation status are provided, together with kits for determining Akt-Ser473 phosphorylation status and methods for improving treatment of a cancer patient that include obtaining a determination of the Akt-Ser473 phosphorylation status of the cancer.

18 Claims, 11 Drawing Sheets

(56) References Cited

PUBLICATIONS

Jacinto E. et al. "SIN1/MIP1 maintains rictor-mTOR complex integrity and regulates Akt phosphorylation and substrate specificity" Cell 2006;127(1):125-37.

Kirkegaard T. et al. "AKT activation predicts outcome in breast cancer patients treated with tamoxifen" J Pathol 2005;207(2):139-46.

Liang, K.E. et al., "Differential roles of phosphoinositide-dependent protein kinase-1 and Akt1 expression and phosphorylation in breast cancer cell resistance to paclitaxel, doxorubicin, and gemcitabine", Mol Pharmacol, Sep. 2006, 70(3):1045-1052.

MacKeigan, J.P. et al., "Inactivation of the antiapoptotic phosphatidylinositol 3-kinase-Akt pathway by the combined treatment of taxol and mitogen-activated protein kinase kinase inhibition" Clin Cancer Res 2002;8(7):2091-9.

Mamounas, E.P. et al. "Paclitaxel after doxorubicin plus cyclophosphamide as adjuvant chemotherapy for node-positive breast cancer: results from NSABP B-28" J Clin Oncol 2005;23(16):3686-96.

Perez-Tenorio G. et al., "Activation of AKT/PKB in breast cancer predicts a worse outcome among endocrine treated patients" Br J Cancer 2002;86(4):540-5.

Pritchard K.I. et al. "HER-2 and topoisomerase II as predictors of response to chemotherapy" J Clin Oncol 2008;26(5):736-44.

Stal, O. et al., "Akt kinases in breast cancer and the results of adjuvant therapy", Breast Cancer Research, Jan. 2003, 5(2):R37-R44, XP002964821.

Tan, A.R., et al. "Evaluation of biologic end points and pharmacokinetics in patients with metastatic breast cancer after treatment with erlotinib, an epidermal growth factor receptor tyrosine kinase inhibitor" J Clin Oncol 2004;22(15):3080-90.

Tokunaga, E. et al., "The association 17-27 between Akt activation and resistance to hormone therapy in metastatic breast cancer", European Journal of Cancer, Mar. 2006, 42(5):629-635, XP025104813.

Xie and Liu , "Adjusted Kaplan-Meier estimator and log-rank test with inverse probability of treatment weighting for survival data" Stat Med 2005;24(20):3089-110.

Yang, Sherry X. et al., "Akt phosphorylation at Ser473 predicts benefit of paclitaxel chemotherapy in node-positive breast cancer", J Clin Oncol, May 2010, 28(18):2974-2981, XP009138141.

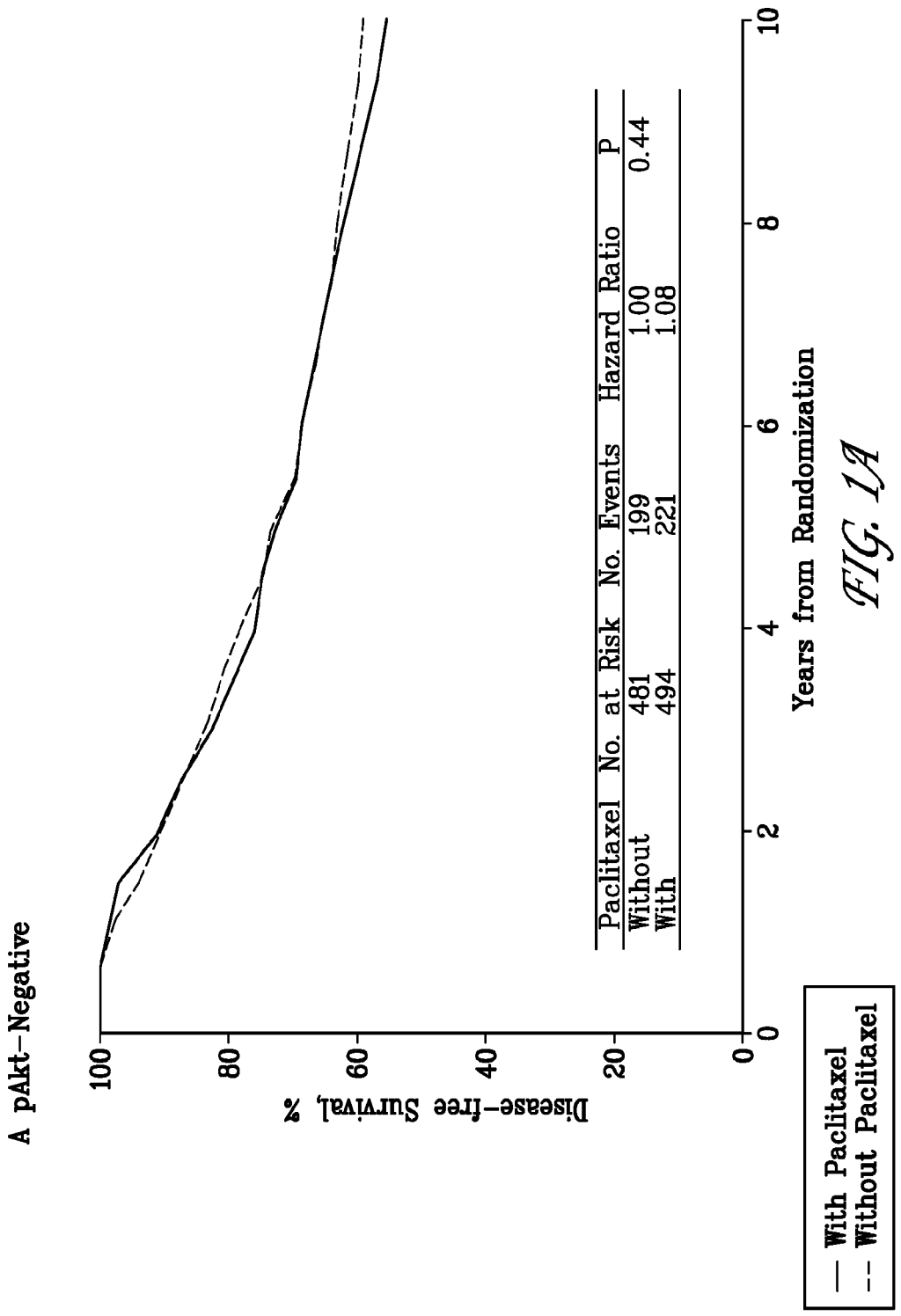

SEQUENCE LISTING

<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      pAKT peptide
<220> FEATURE:
<221> NAME/KEY: MOD_RES
<222> LOCATION: (11)..(11)
<223> OTHER INFORMATION: pSerine473
<220> FEATURE:
<223> OTHER INFORMATION: C-term NH2

<400> SEQUENCE: 1

Ser Glu Arg Arg Pro His Phe Pro Gln Phe Ser Tyr Ser Ala
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      control peptide

<400> SEQUENCE: 2

Ser Glu Arg Arg Pro His Phe Pro Gln Phe Ser Tyr Ser Ala
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: pSerine473
<220> FEATURE:
<223> OTHER INFORMATION: C-term NH2

<400> SEQUENCE: 3

Cys Ser Glu Arg Arg Pro His Phe Pro Gln Phe Ser Tyr Ser Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 4

Cys Ser Glu Arg Arg Pro His Phe Pro Gln Phe Ser Tyr Ser Ala
1               5                   10                  15

AKT PHOSPHORYLATION AT SER473 AS AN INDICATOR FOR TAXANE-BASED CHEMOTHERAPY

CROSS-REFERENCE TO RELATED APPLICATIONS

This application is the National Stage of International Patent Application No. PCT/US2010/035816, filed May 21, 2010, which claims the benefit of U.S. Provisional Patent Application No. 61/180,558, filed May 22, 2009, the disclosures of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Apr. 5, 2013, is named NIHA-0469_SL.txt and is 1,676 bytes in size.

TECHNICAL FIELD

The application relates to Akt phosphorylation at serine 473 site (pAkt), to methods and kits fix identifying pAkt-positive human tumors and to improving methods of treating patients that have such tumors.

BACKGROUND

Adjuvant chemotherapy significantly improves disease-free and overall survival in early stage breast cancer. "Effects of chemotherapy and hormonal therapy for early breast cancer on recurrence and 15-year survival: an overview of the randomised trials" Lancet 2005; 365(9472):1687-717. Anthracycline-containing regimens (e.g., doxorubicin and others), as compared with non-anthracycline-containing regimens, have been shown to further reduce recurrence and mortality rates. Over the past decades, taxanes, such as paclitaxel and docetaxel, have also emerged as effective chemotherapy agents for breast cancer and other malignancies. The addition of taxanes into the adjuvant breast cancer setting resulted in a significant improvement for disease-free survival and/or overall survival. De Laurentiis M. Cancello G, D'Agostino D, et al. "Taxane-based combinations as adjuvant chemotherapy of early breast cancer: a meta-analysis of randomized trials" J Clin Oncol 2008: 26(1):44-53. The B-28 randomized clinical trial from the National Surgical Adjuvant Breast and Bowel Project (NSABP), for example, compared the treatment outcome achieved by sequential addition of paclitaxel to a doxorubicin plus cyclophosphamide regimen, compared with doxorubicin plus cyclophosphamide alone, in patients with axillary node positive breast cancer. The addition of paclitaxel alter doxorubicin plus cyclophosphamide was found to significantly improve disease-free survival but not overall survival. Mamounas E P, Bryant J, Lembersky B, et al. "Paclitaxel after doxorubicin plus cyclophosphamide as adjuvant chemotherapy for node-positive breast cancer: results from NSABP 8-28" J Clin Oncol 2005; 23(16):3686-96.

However, not all patients benefit from treatment with taxanes. Moreover, treatment with these drugs is expensive, and causes substantial morbidity and occasional life-threatening toxic effects, including neuropathy, neutropenia, leucopenia, anemia, hair loss, muscle/joint pain, nausea, vomiting and diarrhea. Other less frequent serious side effects include abnormal sensations (burning or tingling), thrombocytopenia and blood clotting problems, sores in the mouth or intestinal tract, change in electrocardiogram, and hypotension. Given these facts, the identification of biomarkers that reliably predict which patients are likely to benefit from treatment with a taxane is of critical importance.

Currently, no biomarkers predictive of outcome in patients who received taxane-based chemotherapy have been identified. Recent meta-analyses found a significant disease-free benefit for women with breast cancer who received taxane-based therapy regardless of hormonal receptor status and HER2 status (DeLaurentis, et al, supra; Pritchard K I, Messersmith H, Elavathil L, Trudeau M, O'Malley F, Dhesy-Third B "HER-2 and topoisomerase II as predictors of response to chemotherapy" J Clin Oncol 2008; 26(5):736-44), but no biomarkers have been identified that are predictive of treatment outcome with taxanes.

Akt is a serine/threonine protein kinase (also known as protein kinase B) that has been implicated in the pathogenesis of cancer, and essential cellular processes including metabolism, cell growth, proliferation, cell cycle progression, survival and differentiation. Bhaskar P T, Hay N "The two TORCs and Akt" Dev Cell 2007; 12(4):487-502. Recent pre-clinical studies reported that Akt-Ser473 is phosphorylated by SIN-1-rictor-mTOR complex, which is required fir the cellular function such as survival (Jacinto E, Facchinetti V, Liu D, et al. "SIN1/MIP1 maintains rictor-mTOR complex integrity, and regulates Akt phosphorylation and substrate specificity" Cell 2006; 127(1):125-37) and actin cytoskeletal reorganization. Importantly, paclitaxel inhibits Akt phosphorylation at serine 473 and reduces the survival cancer cells. MacKeigan J P, Taxman D J, Hunter D, Earp H S, 3rd, Graves L M, Ting J P "Inactivation of the antiapoptotic phosphatidylinositol 3-kinase-Akt pathway by the combined treatment of taxol and mitogen-activated protein kinase kinase inhibition" Clin Cancer Res 2002; 8(7):2091-9; Asakuma J, Sumitomo M, Asano T, Asano T, Hayakawa M "Selective Akt inactivation and tumor necrosis actor-related apoptosis-inducing ligand sensitization of renal cancer cells by low concentrations of paclitaxel" Cancer Res 2003: 63(6):1365-70. Phosphorylation of Akt at serine 473 (pAkt) in breast cancer patients has been associated with tumor relapse with distant metastasis (Perez-Tenorio G, Stal O "Activation of AKT/PKB in breast cancer predicts a worse outcome among endocrine treated patients" Br J Cancer 2002; 86(4):540-5), and poor outcome to hormonal therapy (Kirkegaard T, Witton C J McGlynn L M, et al. "AKT activation predicts outcome in breast cancer patients treated with tamoxifen" J Pathol 2005; 207(2):139-46). However, prior to the studies reported herein, a link between the pAkt status of cancers to the efficacy of taxane treatment has not been evaluated.

SUMMARY

The instant application derives from the important discovery that pAkt status can be used as a biomarker and indication for treatment with taxane chemotherapy. In particular, disclosed herein are methods of determining whether a subject having cancer is likely to benefit from a treatment regimen that contains treatment with a taxane compound comprising obtaining a determination of whether tissue from the subject's cancer is pAkt positive.

Also provided are unproved methods of treating a cancer in a subject in which the cancer may be treated by administration of a taxane. These methods involve the steps of obtaining a determination of whether said cancer is pAkt positive and, upon a determination that the cancer is pAkt positive, indicating that the subject is likely to benefit from treatment with a taxane compound.

Another embodiment of the invention relates to kits for determining whether a patient is likely to benefit from treatment with a taxane compound. In one embodiment, such kits include means for determining whether tumor cells from said patient's cancer are pAkt positive, wherein a determination that said cancer pAkt positive indicates that the patient is likely to benefit from treatment with a taxane compound. Some of the kits comprise a pAkt specific antibody. One embodiment is a kit having an anti-pAkt antibody specific to a phosphorylated peptide consisting of a pAKT sequence SERRPHFPQF{pSerine473}YSA-NH2 (SEQ ID NO: 1).

A further embodiment of the invention relates to an improvement in methods of treating cancer in a patient that comprise the use of chemotherapy with an anthracycline and cyclophosphamide followed by treatment with a taxane compound. In particular, the improvement comprising the step of obtaining a determination of whether said cancer is pAkt positive.

DETAILED DESCRIPTION OF ILLUSTRATIVE EMBODIMENTS

Figure 1B:
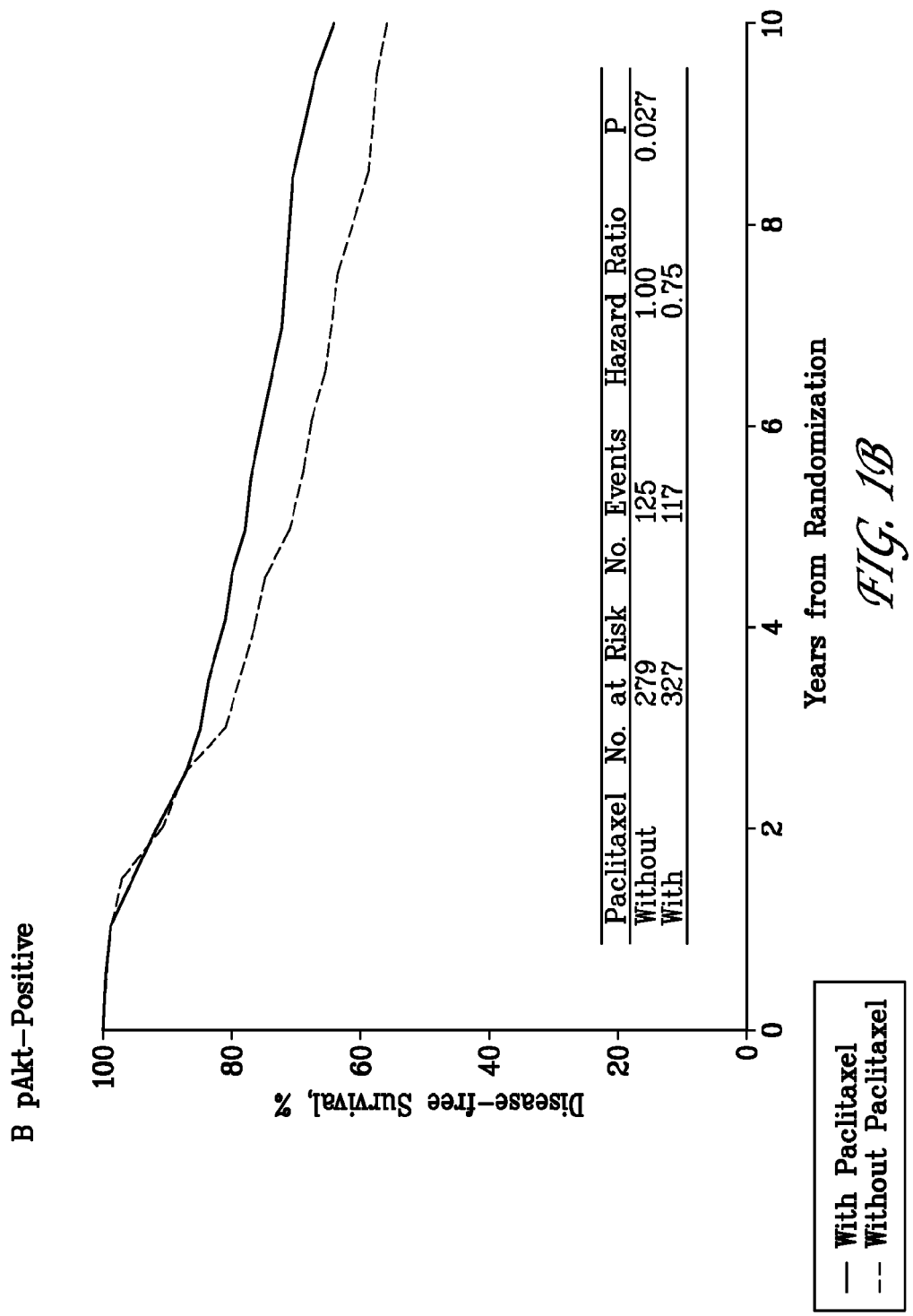
FIG. 1 (A-C) show the disease-free survival rates for pAkt positive and pAkt negative patients, with and without treatment with paclitaxel.

Taxanes are diterpene compounds, related to compounds produced by the plants of the genus *Taxus* (yews). As their name suggests, taxane compounds were first derived from natural sources, but some have been synthesized artificially. FDA-approved taxane compounds include paclitaxel and docetaxel. Taxanes, which function as mitotic inhibitors, have a unique way of preventing the growth of cancer cells by affecting cell structures called microtubules, which play an important role in cell function. In normal cell growth, pre-existing microtubules, which support cell shape and act as "highways" for transport of materials inside the cell, are completely rearranged into a machine called the spindle when a cell starts dividing. Once the cell stops dividing, the spindle disappears and a microtubule network reappears. These rearrangements require rapid microtubule disassembly and reassembly. Taxanes stop microtubules from breaking down and rearranging properly. In addition, they cause too many microtubules to form and to form in the wrong places. All this prevents cancer cells from growing and dividing in an efficient manner.

The present inventors have found that patients having tumors that exhibit phosphorylation of Akt at Ser473 (i.e., are "pAkt positive") are more likely to benefit from a treatment regimen that includes treatment with a taxane compound than patients having tumors that are not pAkt positive. As used herein, the term "likely to benefit" means that the patients have an increased probability of disease-free survival, and possibly an increase in overall survival, as compared to patients having p-Akt positive tumors that do not receive treatment with a taxane compound. Preferably, the increased probability of disease-free survival is at least about 5%, preferably 10%, more preferably at least about 20% and still more preferably, at least about 25% and even still more preferably, about 26%. The increased probability of overall survival is from 5% to 20%.

One embodiment of the invention relates to the use of a tumor's pAkt status as a predictive indicator of the likely benefit from treatment with a taxane compound. Accordingly, such methods entail obtaining a determination of whether the tumor tissue is pAkt positive or pAkt negative in preferred embodiments, the pAkt status is determined by immunodetection (i.e. antibody-based identification). A variety of different immunodetection techniques may be used to allow for detection of pAkt. In general, suitable immunodetection methods involve at least 3 steps, including: obtaining a specimen, suspected of containing pAkt, contacting the specimen, or a derivative of the specimen with at least one antibody that specifically binds to pAkt, and detecting pAkt-specific antibody bound to the specimen.

As will be apparent to those of skill in the art, the general immunodetection scheme described in the preceding paragraph can be carried out in a variety of ways. For example, immunodetection methods such as western blot, ELISA, immunoprecipitation, flow cytometry, immunohistochemistry, and the like may be used to detect pAkt-positive cells in a specimen from the tumor.

The specimen used in the described immunodetection methods can be derived from any tumor tissue or tumor cells from a patient having a cancer. The specimen or tumor cells can be derived from a tissue biopsy, blood, or body fluid.

There are a number of antibody detection processes that may be used to carry out these detection methods.

detection can be accomplished using a pAkt-specific primary antibody, followed by detection with a labeled secondary antibody;

a labeled pAkt-specific primary antibody could be used for detection; and/or

Fab or F(ab')$_2$ can be used for detection.

Detection of bound antibodies can also be carried out in a variety of ways, such as fluorescence-based detection, enzyme-based detection, or radiolabeled detection.

Of course, other antigen-binding proteins could also be used to detect pAkt, such as anti-pAkt Fabs, F(ab')$_2$, and the like. Detection of bound antibodies can also be carried out in a variety of ways, such as fluorescence-based detection, enzyme-based detection, or radiolabled detection. Other suitable means of antibody detection will be understood by those of skill in the art. For a general description of the assays and antibody based detection methods described herein, see e.g., C. Janeway, et al, Immunobiology (5th ed. 2001).

Further embodiments of the invention relate to improved methods of treating patients having cancer comprising obtaining a determination of whether the cancer is pAkt positive, and upon a determination that it is pAkt positive, indicating that a patient is likely to benefit from treatment with a taxane compound. Methods of administering taxane compounds are known in the art. For example, Taxol® paclitaxel injection, marketed by Bristol-Myers Squibb (NDA 020262) is approved for use in treating breast cancer and ovarian cancer and is widely used for treatment of other cancer types. Taxotere® injectable preparation of docetaxel is marketed by Sanofi-Aventis (NDA 020449) for the treatment of breast, colorectal, lung, ovarian, liver, renal, head and neck, prostate and stomach cancers and melanoma. Administration procedures and dosage protocols are described on the FDA-approved package labeling for these products (incorporated by reference herein) or are otherwise known to those of ordinary skill in the art.

Treatment regimens that include administration of a taxane compound may be applicable as part of adjuvant chemotherapy, for example, after surgical removal of a primary tumor in a patient whose tumor status (size, grade, etc.) or other risk factors (for example, age, prior history, the presence of tumor cells in draining lymph nodes, etc.) renders them suitable candidates for chemotherapy. Treatment regimens with a taxane compound are used in patients suffering from metastatic cancer. Additionally, treatment regimens utilizing a taxane compound may be instituted in a neoadjuvant setting, where the cancer may initially be too big for surgery or otherwise inoperable prior to treatment with a taxane compound.

Other embodiments of the invention relate to kits useful in the identification and treatment of patients that may benefit from treatment with taxane compounds. Such kits may comprise means for determining whether tissue (either frozen or formalin-fixed and paraffin-embedded) from a patient's cancer is pAkt positive, wherein a determination that the tissue is pAkt positive indicates that the patient is likely to benefit from treatment with a taxane compound. Suitable means for determining whether the cancer is pAkt positive include the various immunodetection methods described above as well as those utilized in the examples described below. One embodiment of a kit for determining whether a patient is likely to benefit from treatment with a taxane compound comprises a pAkt-specific antibody. Such antibodies (either polyclonal or monoclonal) are commercially available, for example, from Cell Signaling Technology, Beverly, Mass. The kit may further include a stain suitable for detecting binding of said antibody to pAkt in the tissue, and guidelines for interpretation and "scoring" of the sample as pAkt positive or pAkt negative. In some instances, scoring may be performed according to traditional methods utilized by pathologists. In other instances, the kit may be adapted for use with digital imaging equipment to facilitate the detection of binding of the antibody to tissue and quantitative scoring of the sample. Kits may also contain a slide containing appropriate positive and negative control cells or tissues. Guidelines may also be provided providing instructions for optimizing antigen retrieval and preparation of samples for performing pAkt immunohistochemistry.

Additionally, kits may simply include diagnosis that treatment with a taxane compound may be indicated upon a determination that the cancer is pAkt positive according to the FDA labeling for the taxane compound being utilized.

Preferred aspects of the invention are set forth in the following examples. While the present invention has been described with specificity in accordance with certain of its preferred embodiments, the invention is not so limited.

EXAMPLES

We designed and conducted a study to correlate Akt phosphorylation with clinical outcome through the primary tumor specimens from the National Surgical Adjuvant Breast and Bowel Project B-28 trial. We tested the hypothesis that phosphorylation of Akt at serine 473 ("pAkt") predicts a benefit for women with node-positive breast cancer from the sequential addition of paclitaxel after adjuvant doxorubicin plus cyclophosphamide chemotherapy.

Production of an Antibody Against a Peptide from Akt

Two peptides were generated and isolated: the phospho-Akt (Ser473) peptide having the sequence SERRPHFPQF{pSerine473}YSA-NH2 (SEQ ID NO: 1) and the control peptide having the sequence SERRPHFPQF-SYSA-NH2 (SEQ ID NO: 2). After the third immunization, the tested sera from all five Balb/c mice showed differential recognizing, phospho-Akt-Ser473 (Table 1 and Table 2). Western blot analysis of the polyclonal sera from mice #1 and 2 was performed, showing that there was a pAkt band at 60 kpa from mouse #1.

The monoclonal antibodies from the clones recognize phospho-Akt-Ser473 peptide but not non-phospho-Akt-Ser473 is selected. The clones that recognize a single 60 kDa band by western blot are further selected and expanded. Lastly, the selected clones are tested by immunohistochemistry on paraffin-embedded tumor sections known to express and not to express pAkt-Ser473. This also includes the use of phospho-Akt-Ser473 peptide as a blocking agent to further evaluate the specificity of the monoclonal antibodies. Characterized monoclonal antibodies are utilized to construct pAkt-Ser473 detection kit.

TABLE 1

ELISA for pre-immunization serum (negative control):

| Animal | 1:1,000 | 1:3,000 | 1:9,000 | 1:27,000 | 1:81,000 | Blank | Titer | Coating |
|---|---|---|---|---|---|---|---|---|
| No. 1 | 0.065 | 0.054 | 0.085 | 0.065 | 0.083 | 0.082 | <1:1k | 89239-2 |
|  | 0.077 | 0.069 | 0.075 | 0.083 | 0.095 | 0.098 | <1:1k | 89239-3 |
| No. 2 | 0.077 | 0.086 | 0.083 | 0.107 | 0.092 | 0.073 | <1:1k | 89239-2 |
|  | 0.074 | 0.072 | 0.081 | 0.075 | 0.082 | 0.109 | <1:1k | 89239-3 |
| No. 3 | 0.095 | 0.081 | 0.101 | 0.102 | 0.102 | 0.093 | <1:1k | 89239-2 |
|  | 0.087 | 0.078 | 0.094 | 0.084 | 0.104 | 0.092 | <1:1k | 89239-3 |
| No. 4 | 0.075 | 0.064 | 0.085 | 0.065 | 0.083 | 0.107 | <1:1k | 89239-2 |
|  | 0.067 | 0.068 | 0.085 | 0.073 | 0.095 | 0.096 | <1:1k | 89239-3 |
| No. 5 | 0.085 | 0.074 | 0.081 | 0.088 | 0.092 | 0.087 | <1:1k | 89239-2 |
|  | 0.091 | 0.084 | 0.076 | 0.082 | 0.077 | 0.092 | <1:1k | 89239-3 |

TABLE 2

ELISA for antiserum after 3$^{rd}$ Immunization:

| Animal | 1:1,000 | 1:3,000 | 1:9,000 | 1:27,000 | 1:81,000 | Blank | Titer | Coating |
|---|---|---|---|---|---|---|---|---|
| No. 1 | 3.311 | 3.311 | 3.082 | 2.22 | 1.164 | 0.075 | <1:81k | 89239-2 |
|  | 3.009 | 3.082 | 2.485 | 1.335 | 0.577 | 0.078 | <1:81k | 89239-3 |

TABLE 2-continued

ELISA for antiserum after 3rd Immunization:

| Animal | 1:1,000 | 1:3,000 | 1:9,000 | 1:27,000 | 1:81,000 | Blank | Titer | Coating |
|---|---|---|---|---|---|---|---|---|
| No. 2 | 3.154 | 2.97 | 2.18 | 1.175 | 0.503 | 0.062 | <1:81k | 89239-2 |
|  | 2.956 | 2.129 | 1.13 | 0.452 | 0.219 | 0.074 | <1:81k | 89239-3 |
| No. 3 | 3.475 | 3.132 | 2.698 | 2.15 | 1.372 | 0.064 | <1:81k | 89239-2 |
|  | 2.943 | 2.906 | 2.501 | 1.514 | 0.673 | 0.076 | <1:81k | 89239-3 |
| No. 4 | 3.182 | 2.751 | 1.958 | 1.067 | 0.451 | 0.08 | <1:81k | 89239-2 |
|  | 2.165 | 1.048 | 0.568 | 0.146 | 0.093 | 0.078 | <1:9k | 89239-3 |
| No. 5 | 3.264 | 3.118 | 2.361 | 1.334 | 0.584 | 0.111 | <1:81k | 89239-2 |
|  | 2.797 | 1.848 | 0.959 | 0.397 | 0.213 | 0.109 | <1:27k | 89239-3 |

Patients

Patient eligibility and enrollment to the National Surgical Adjuvant Breast and Bowel Project B-28 trial are described in Mamounas E P, Bryant J, Lembersky B, et al. "Paclitaxel after doxorubicin plus cyclophosphamide as adjuvant chemotherapy for node-positive breast cancer: results from NSABP B-28" *J Clin Oncol* 2005; 23(16):3686-96, incorporated herein by reference. Three thousand sixty women with node-positive breast cancer who has completed surgery with free margins plus axillary node dissection were randomly assigned to either four cycles of adjuvant doxorubicin (60 mg/m$^2$) plus cyclophosphamide (600 mg/m$^2$) only or followed by additional four cycle of paclitaxel (225 mg/m$^2$) treatment. Eligible patients signed an approved informed consent which includes tissue collection and research use of collected tissue conforming to federal and institutional guidelines. In this study, the biomarker protocol for the evaluation of Akt phosphorylation in association with disease-free survival and overall survival in patients with node-positive breast cancer treated with either adjuvant doxorubicin plus cyclophosphamide only or followed by paclitaxel was approved by the Institutional Review Boards of the National Cancer institute (Bethesda, Md.) and the National Surgical Adjuvant Breast and Bowel Project (Pittsburgh, Pa.).

Breast Cancer Specimen Collection, Tissue Microarray Construction, and Determination of Her2 Status and Estrogen Receptor Status The tissue microarray blocks were constructed from 1982 cases that had archived primary tumor blocks, which were representative of two treatment arms and tissue characteristics, and collected prospectively from patients who participated in NSABP B28 trial. HER2 status on the microarray sections were determined by the NSABP central pathology laboratory using PathVision fluorescent in situ hybridization (FISH) assay according to the FDA approved protocol per the manufacturer (Vysis, Downers Grove. Ill.). Data were expressed as the number of HER2 genes per chromosome 17 centromere: tumors with a ratio of $\geq 22$ were classified as HER2-positive, and those with a ratio of <2 were defined as HER2-negative. Estrogen receptor status in tissue microarray sections were also determined by the NSABP central pathology laboratory by immunohistochemistry according to the FDA approved protocol provided by DAKO (PharmDx kit; Carpinteria, Calif.). A positive result (tumor cell nuclear staining) for ER is defined as a total score (ranging from 0, 2-8) of $\geq 3$. The total score is the sum of a proportion score from 0 to 5 and an intensity score of 0 to 3.

Immunohistochemical Analysis for Akt Phosphrylation at Ser473

Akt phosphorylation status on formalin-fixed and paraffin-embedded primary tumors of the B-28 trial tissue microarray set was examined by immunohistochemistry with rabbit polyclonal antibodies to pAkt-Ser473 (Cell Signaling Technology, Beverly, Mass.). Antigen retrieval method and concentration of the antibodies was optimized for detection of phosphorylated Akt according to methodology described in Tan A R, et al. "Evaluation of biologic end points and pharmacokinetics in patients with metastatic breast cancer after treatment with erlotinib, an epidermal growth factor receptor tyrosine kinase inhibitor" *J Clin Oncol* 2004; 22(15):3080-90 (incorporated herein by reference).

pAkt status on formalin-fixed paraffin-embedded primary tumors were examined by immunohistochemistry established as previously described (Yang et al JCO, 2010). In brief, epitope retrieval are performed in antigen retrieval buffer (pH10; Dako, Carpinteria, Calif.) and heated in a microwave oven for 15 minutes. Sections will be incubated with rabbitpolyclonal antibody specific to pAkt-Ser473 (Cell Signaling Technology, Beverly, Mass.) in a 1:100 dilution. Binding of the antibody to antigenic sites are amplified using Vectastain Elite avidin-biotin-peroxidase complex kits (Vector Laboratories, Burlingame, Calif.). Breast cancer cell line MDA-MB-468, and a breast cancer specimen that have established levels of pAkt expression are utilized as external positive controls. Negative control are performed using isotype immunoglobulins appropriate to the primary antibody used (Zymed Laboratories, South San Francisco, Calif.). The assay reproducibility has been demonstrated (with a 5.7% covariance of coefficient on three independent pAkt staining in MDA-MB-468 breast cancer cells) (Yang et al, JCO, 2010).

pAkt signal with cytoplasmic, membranous or nuclear staining are analyzed with the assistance of an Automated Cellular Imaging System (ACIS III, Dako, Carpinteria, Calif.) at the National Cancer Institute blinded to all clinical information. The sub-cellular localization of pAkt are documented at the time of captured image analysis. Tissue cores with <5% of invasive tumor cells present are excluded for analysis. The intensity and percentage of stained tumor cells on each core are generated using a free-scoring tool by the digital imaging system. Staining index is determined by percentage multiplied by intensity of staining divided by 100 as previously described. The staining index of >2 will be chosen as pAkt staining positive cutoff as established from the pAkt B-28 study (Yang et al, JCO 2010). This cutoff for positivity includes pAkt staining with a visual staining intensity of 1+, 2+ and 3+.

Sections were incubated with primary antibody in 1 to 100 dilution for 1 hour at room temperature, and binding of the antibody to its antigenic sites was amplified using Vectastain Elite avidin-biotin peroxidase complex kits (Vector Laboratories, Burlingame, Calif.). The antigen-antibody reaction sites were visualized using 3,3-diaminobenzidine for 7 minutes and, subsequently, sections were counterstained with Mayer's hematoxylin. Breast cancer cell line MDA-MB-468 which expresses pAkt, and a breast cancer specimen known to express pAkt were utilized as positive controls. Negative control was performed using isotype immunoglobulins appropriate to the primary antibodies being used (Zymed Laboratories, South San Francisco, Calif.). The immunostained tissue microarray cores with either cytoplasmic or membranous or nuclear signal were analyzed with the assistance of an Automated Cellular Imaging System (DAKO), blinded to all clinical information, after excluding tissue cores with less than 5% of invasive tumor cells present. The staining intensity and percentage of tumor cells on each tissue core was calculated by the digital imaging system. The staining index ranging from 0 to 62.8 reporting levels of Akt phosphorylation at Ser473 was determined by the percentage multiplied by intensity of staining divided by 100 (intensity X percentage/100) in tumor cells, in which the intensity was subtracted from the average tissue readout of three normal tissue cores. These cores serve as the position markers and tissue negative controls for each array slide. The concordance was met from the quality assurance cores in duplicate or triplicate built-in throughout B-28 tissue microarray set; the minor discordance was reconciled. Four cases, each in duplicate, could not be reconciled due to tumor heterogeneity and were excluded from the data analysis. pAkt status was categorized by the staining index of >2 (positive) and ≤2 (negative). The staining index of >2 (range, 0 to 62.8) was arbitrarily chosen as the cutoff for pAkt positivity. Correlation with clinical outcome was performed at the National Surgical Adjuvant Breast and Bowel Project Biostatistical Center.

Statistical Analysis

Differences in the distribution of patient and tumor characteristics between the subset of patients with pAkt measurements and the total population were assessed using the chi-square test. Disease-free survival and overall survival curves by pAkt-positive group and pAkt-negative group treated with or without paclitaxel were estimated with Kaplan-Meier method. The log-rank test was used to assess differences between treatment groups for the outcomes. The events counted in disease-free survival were breast cancer recurrence, second primary cancer (excluding squamous or basal cell carcinoma of the skin, carcinoma in situ of the cervix or lobular carcinoma in situ of the breast) and death from any cause without prior recurrence or second primary cancer. The endpoint included in overall survival was death from any cause. Multivariate Cox proportional hazards modeling was used to compute adjusted disease-free survival and overall survival hazard ratios with 95 percent confidence intervals (CI) for pAkt and prognostic variables. The Wald statistic was used to determine P values for the adjusted hazard ratios and the interaction terms. Kaplan-Meier curves that were adjusted for prognostic variables were determined using the method described by Xie and Liu ("Adjusted Kaplan-Meier estimator and log-rank test with inverse probability of treatment weighting for survival data" *Stat Med* 2005; 24(20):3089-110, incorporated herein by reference). The hazard ratios and P values presented on the adjusted Kaplan-Meier curves were those attained from multivariate Cox modeling.

Results

Outcome, pAkt Expression, and Characteristics of Patients with pAkt Measurement

The B-28 treatment trial results with about 5 years of follow-up have been reported previously. Mamounas et al, supra. With approximate 10 years of follow-up, the results for disease-free survival and overall survival were similar (Table 1, infra). The hazard ratios for disease-free survival and overall survival with the sequential addition of paclitaxel to doxorubicin plus cyclophosphamide were 0.89 (95% CI 0.79 to 0.99; P=0.034) and 0.92 (95% CI 0.81-1.06; P=0.25), respectively.

Primary breast tumors on B-28 tissue microarray were available for analysis from 1581 patients, which represent 52% of the entire B-28 trial population pAkt was expressed in 606/1581 (38%) of breast tumors, in which 279/760 (37%) were M doxorubicin plus cyclophosphamide group, and 327/821 (40%) in doxorubicin plus cyclophosphamide followed by paclitaxel treatment group. The hazard ratios for disease-free survival and overall survival in 1581 patients with pAkt measurement with the addition of paclitaxel to doxorubicin plus cyclophosphamide were 0.94 (95% CI 0.81-1.10; P=0.46) and 0.96 (95% CI 0.79-1.15; P=0.63) with a medication follow-up of 9.1 years.

To confirm that 1581 patients with pAkt measurement in this study were representative of the entire population by treatment group in B-28 trial, we compared age, tumor size, the number of involved lymph nodes, tumor grade, and estrogen receptor status in patients with pAkt measurement and all treated patients (Table 3). There were no significant detectable differences in demographic or prognostic features except for tumor size and tumor glide in the group treated with doxorubicin plus cyclophosphamide alone. In patients with pAkt measurement, approximately 84% of patients received tamoxifen treatment, a proportion similar to that (85%) for the entire B-28 population.

TABLE 3

| | AC | | | | | | | AC-P | | | | | | |
|---|---|---|---|---|---|---|---|---|---|---|---|---|---|---|
| | All Patients (n = 1,529) | | | Patients With pAkt Data (n = 780) | | | | All Patients (n = 1,531) | | | Patients With pAkt Data (n = 821) | | | |
| Variable | No. | % | 95% CI | No. | % | 95% CI | P* | No. | % | 95% CI | No. | % | 95% CI | P* |
| Age (years) | | | | | | | | | | | | | | 80 |
| <59 | 701 | 40.8 | | 996 | 62.4 | | .15 | 788 | 51.5 | | 419 | 51.0 | | |
| <50 | 768 | 90.5 | | 982 | 47.1 | | | 743 | 48.5 | | 401 | 49.0 | | |
| Tumor size† | | | | | | | | | | | | | | .07 |
| ≤2 | 917 | 60.0 | | 417 | 66.0 | | .017 | 694 | 58.4 | | 447 | 54.6 | | |
| 2.3-4.0 | 494 | 32.4 | | 274 | 38.1 | | | 489 | 32.6 | | 292 | 86.6 | | |
| ≥4.3 | 118 | 7.6 | | 87 | 8.8 | | | 186 | 9.0 | | 81 | 9.9 | | |
| Positive lymph nodes | | | | | | | | | | | | | | .07 |
| 1.3 | 1.048 | 69.8 | | 585 | 61.1 | | .08 | 1,068 | 69.8 | | 568 | 69.2 | | |
| 4.3 | 400 | 26.2 | | 203 | 28.2 | | | 395 | 26.8 | | 218 | 78.6 | | |
| ≤10 | 81 | 4.0 | | 32 | 4.2 | | | 69 | 4.4 | | 85 | 4.3 | | |

TABLE 3-continued

| | AC | | | | | | | AC-P | | | | | | |
|---|---|---|---|---|---|---|---|---|---|---|---|---|---|---|
| | All Patients (n = 1,529) | | | Patients With pAkt Data (n = 780) | | | | All Patients (n = 1,531) | | | Patients With pAkt Data (n = 821) | | | |
| Variable | No. | % | 95% CI | No. | % | 95% CI | P* | No. | % | 95% CI | No. | % | 95% CI | P* |
| Tumor grade | | | | | | | .002 | | | | | | | .13 |
| Good | 147 | 9.8 | | 51 | 6.7 | | | 149 | 9.7 | | 70 | 8.5 | | |
| Intermediate | 603 | 39.4 | | 290 | 28.2 | | | 573 | 27.4 | | 308 | 37.5 | | |
| Poor | 685 | 45.5 | | 388 | 91.0 | | | 729 | 47.5 | | 412 | 50.2 | | |
| Unknown | 84 | 5.5 | | 31 | 4.1 | | | 80 | 8.2 | | 81 | 3.8 | | |
| ER Status | | | | | | | | | | | | | | |
| Negative | 518 | 18.7 | | 175 | 38.2 | | .16 | 525 | 34.3 | | 309 | 95.4 | | |
| Positive | 1,019 | 68.3 | | 485 | 63.8 | | | 1,006 | 68.2 | | 522 | 63.5 | | |
| 9-year survival | | | | | | | | | | | | | | |
| Disease free | | 72 | 70-74 | | 70 | 66 to 73 | | | 78 | 73 to 78 | | 73 | 69 to 76 | |
| Overall | | 85 | 83-87 | | 83 | 61 to 85 | | | 85 | 84 to 87 | | 84 | 81 to 85 | |
| 10-year survival | | | | | | | | | | | | | | |
| Disesse free | | 68 | 55-60 | | 55 | 52 to 60 | | | 62 | 59 to 64 | | 66 | 54-60 | |
| Overall | | 71 | 60-74 | | 71 | 67 to 74 | | | 74 | 72 to 78 | | 72 | 69-75 | |

Abbreviations:
NSABP, National Surgical Adjuvant Breast and Project;
pAkt, Aks-5aj473 phosphorylation;
AC, doxorubicin plus cyclophosphamide;
AC-P, AC followed by paclitaxel;
ER, estrogen receptor.
"X" goodness of fit test using all 8-28 patients as the expected distribution.
†Tumor size was unknown for two patients in the AC group and one in the AC-P group.

Paclitaxel and Akt-Ser473 Phosphorylation Status

Disease-free survival and overall survival among patients who did or did not receive paclitaxel were analyzed according to pAkt status as established by immunohistochemistry (FIG. 1). Among 975 patients with pAkt-negative cancer, the disease-free survival rate was similar in those treated with and without the addition of paclitaxel (FIG. 1A; hazard ratio, 1.08; P=0.44). However, in 606 patients with pAkt positive cancer, the sequential addition of paclitaxel significantly increased disease-free survival as compared with doxorubicin plus cyclophasphomide treatment alone (FIG. 1B; hazard ratio, 0.75; P=0.027). There was no overall survival difference between treatment groups in patients with pAkt-negative cancer (hazard ratio, 1.04, P=0.74), or statistically significant difference in patients with pAkt-positive cancer (hazard ratio, 0.83; P=0.226).

To evaluate the potential interaction between pAkt status and treatment for disease-free survival, we tested the statistical significance of the interaction term in a proportional hazards model adjusted for age, tumor grade, tumor size, number of positive nodes, estrogen-receptor status and HER2 status.

TABLE 4

| | Diesease-Free Survival | | | |
|---|---|---|---|---|
| Variable | HR | 95% CI | p | P for Treatment Interaction* |
| pAkt group treatment assignment | | | — | .050 |
| Negative AC | 1.00 | | | |
| Negative AC followed by paclitaxel | 1.03 | 0.86 to 1.25 | | |
| Positive AC | 1.18 | 0.92 to 1.45 | | |
| Positive AC followed by paclitaxel | 0.60 | 0.70 to 1.10 | | |

TABLE 4-continued

| | Diesease-Free Survival | | | |
|---|---|---|---|---|
| Variable | HR | 95% CI | p | P for Treatment Interaction* |
| Age, years | | | .57 | .82 |
| <50 | 1.00 | | | |
| ≥50 | 0.96 | 0.82 to 1.12 | | |
| Tumor size† | | | .001 | .22 |
| ≤2 | 1.00 | | | |
| ≤14.0 | 1.22 | 1.03 to 1.44 | | |
| ≤4.1 | 1.55 | 1.20 to 1.99 | | |
| Positive Lymph nodes | | | <.0001 | .54 |
| 1-3 | 1.00 | | | |
| 4-9 | 1.81 | 1.54 to 2.14 | | |
| ≥10 | 2.46 | 1.80 to 3.35 | | |
| Tumor grade | | | .04 | .35 |
| Good | 1.00 | | | |
| Intermediate | 1.52 | 1.54 to 2.14 | | |
| Poor | 1.57 | 1.08 to 2.27 | | |
| Unknown | 1.04 | 0.80 to 1.82 | | |
| ERstatus | | | <.0001 | .42 |
| Negative | 3.00 | | | |
| Positive | 0.59 | 0.58 to 0.84 | | |
| HER2 status | | | .07 | .25 |
| Negative | 1.00 | | | |
| Positive | 1.27 | 1.03 to 1.55 | | |
| Unknown | 1.01 | 0.90 to 1.26 | | |

Abbreviations:
AC, doxorubicin plus cyclophosphamide;
HR, hazard ratios pAkt, Akt-Ser473 phosphorylation,
EB, estrogen receptor,
HER2, human epidermal growth factor receptor 2.
*p for treatment-by-factor interaction.
†Three patients with unknown tumor size excluded (two in the AC arm and one in the AC followed by paclitaxel group).

Figure 1C:
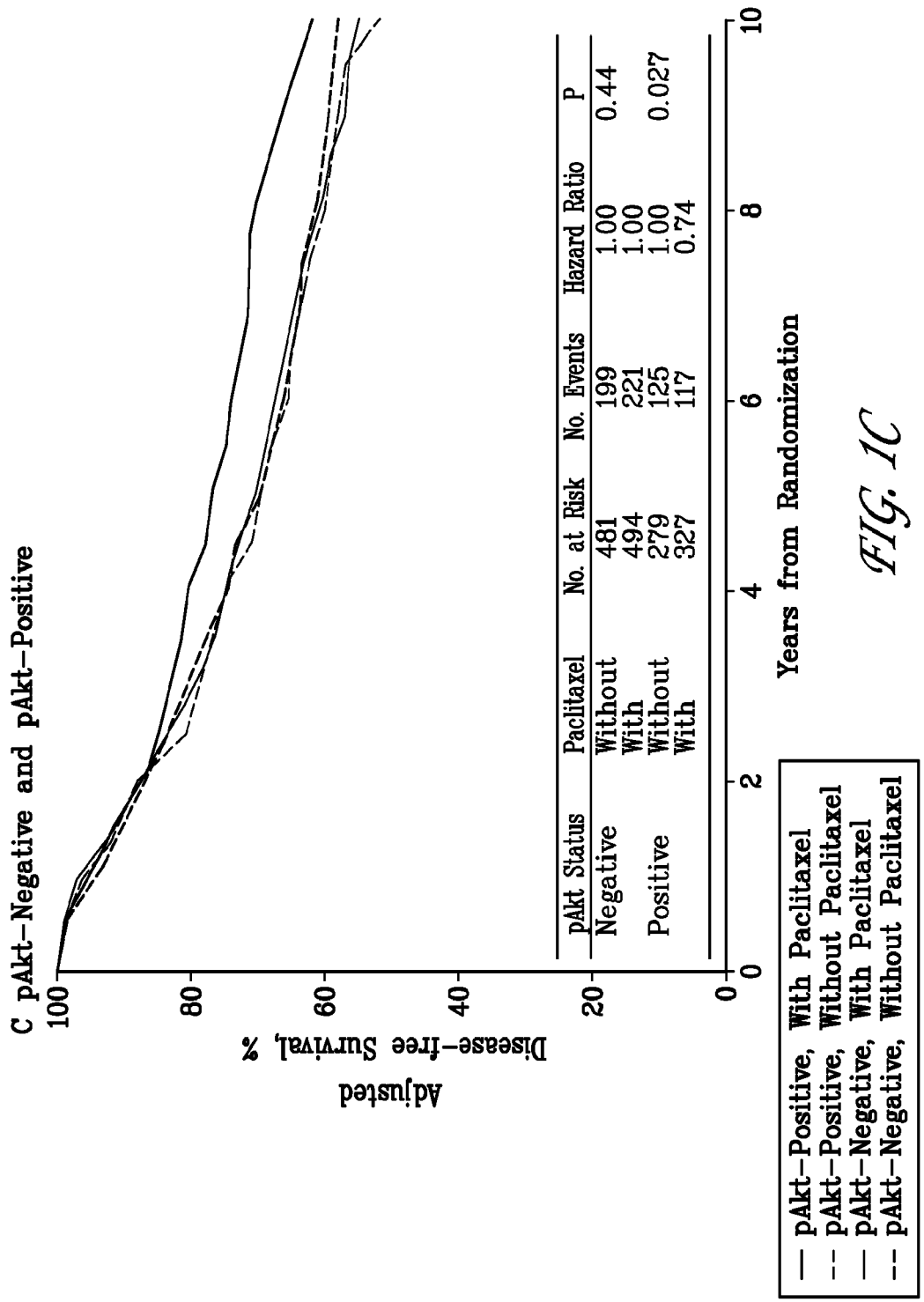

The formal test of the interaction between treatment and pAkt status reached borderline statistical significance (P=0.056). Furthermore, to investigate the influence of some imbalances such as tumor grade, tumor size and other potential prognostic factors including age, number of positive nodes, estrogen receptor status and HER2 status on our results, we conducted a multivariate analysis using the proportional-hazards model with data stratified according to disease-free interval. FIG. 1C shows the adjusted Kaplan-Meir survival curves representing four populations stratified by treatment and pAkt status. When comparing the adjusted survival curves for those treated with or without paclitaxel, the adjusted hazard ratio among those with pAkt negative cancer was 1.02 (P=0.81). In contrast, the adjusted hazard ratio for patients treated with or without paclitaxel among patients with pAkt positive breast cancer was 0.74 (P=0.02), indicating that those who received the sequential addition of paclitaxel had 26% improvement in disease-free survival.

Figure 2A:
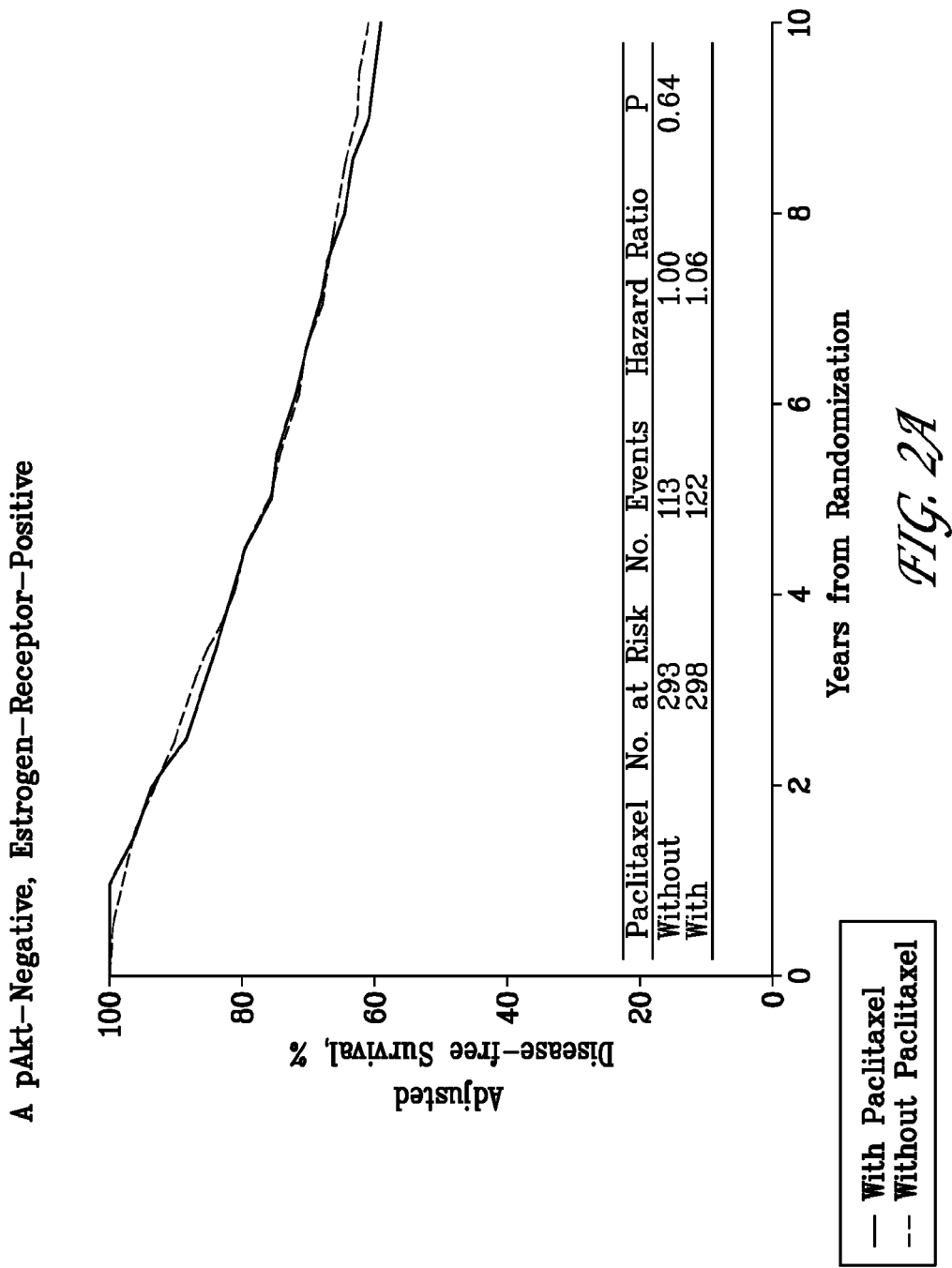
FIG. 2 (A-D) provides the adjusted Kaplan-Meier plots for disease-free survival in patients with pAkt-negative and pAkt-positive cancer stratified by estrogen receptor status.
Figure 2B:
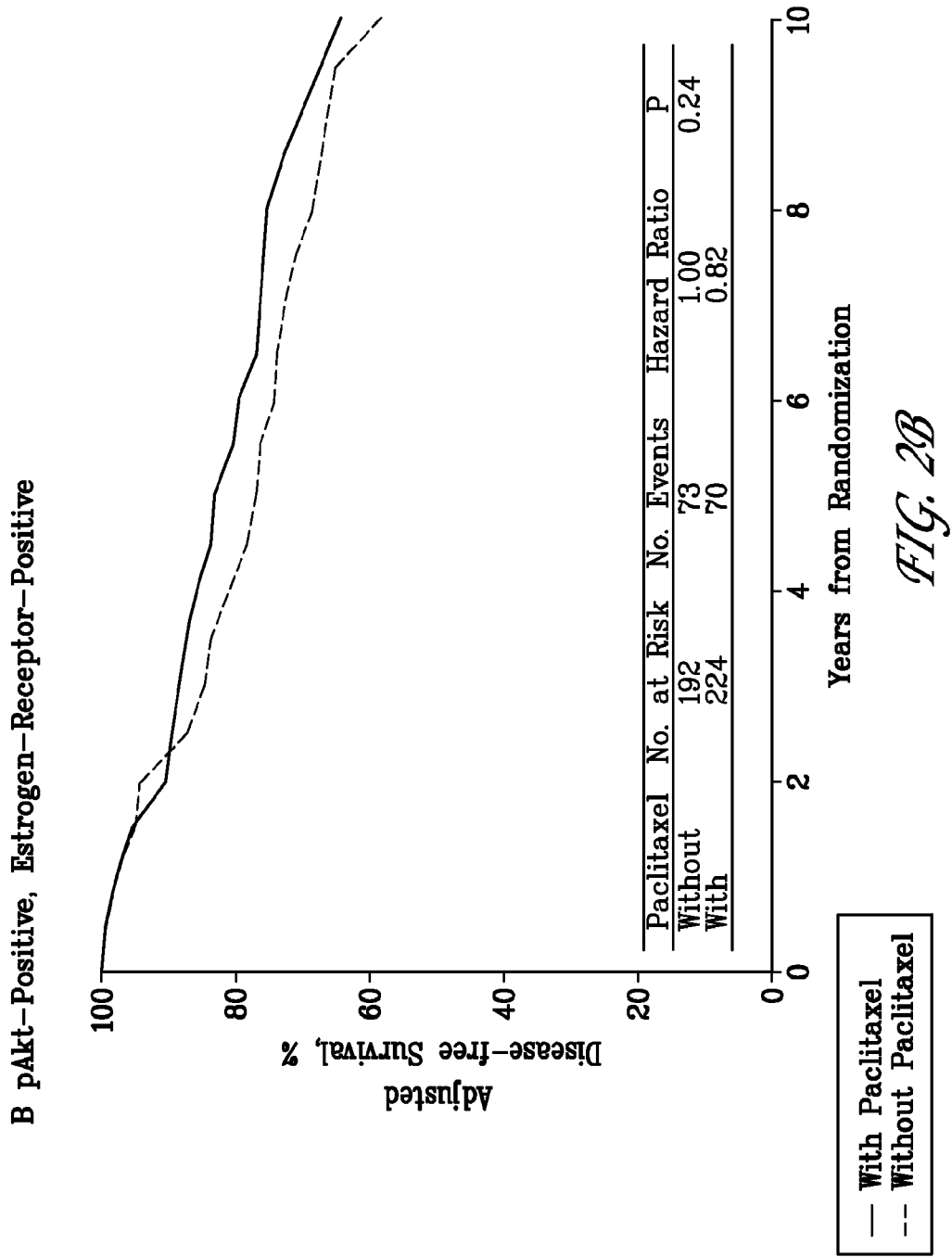
Figure 2C:
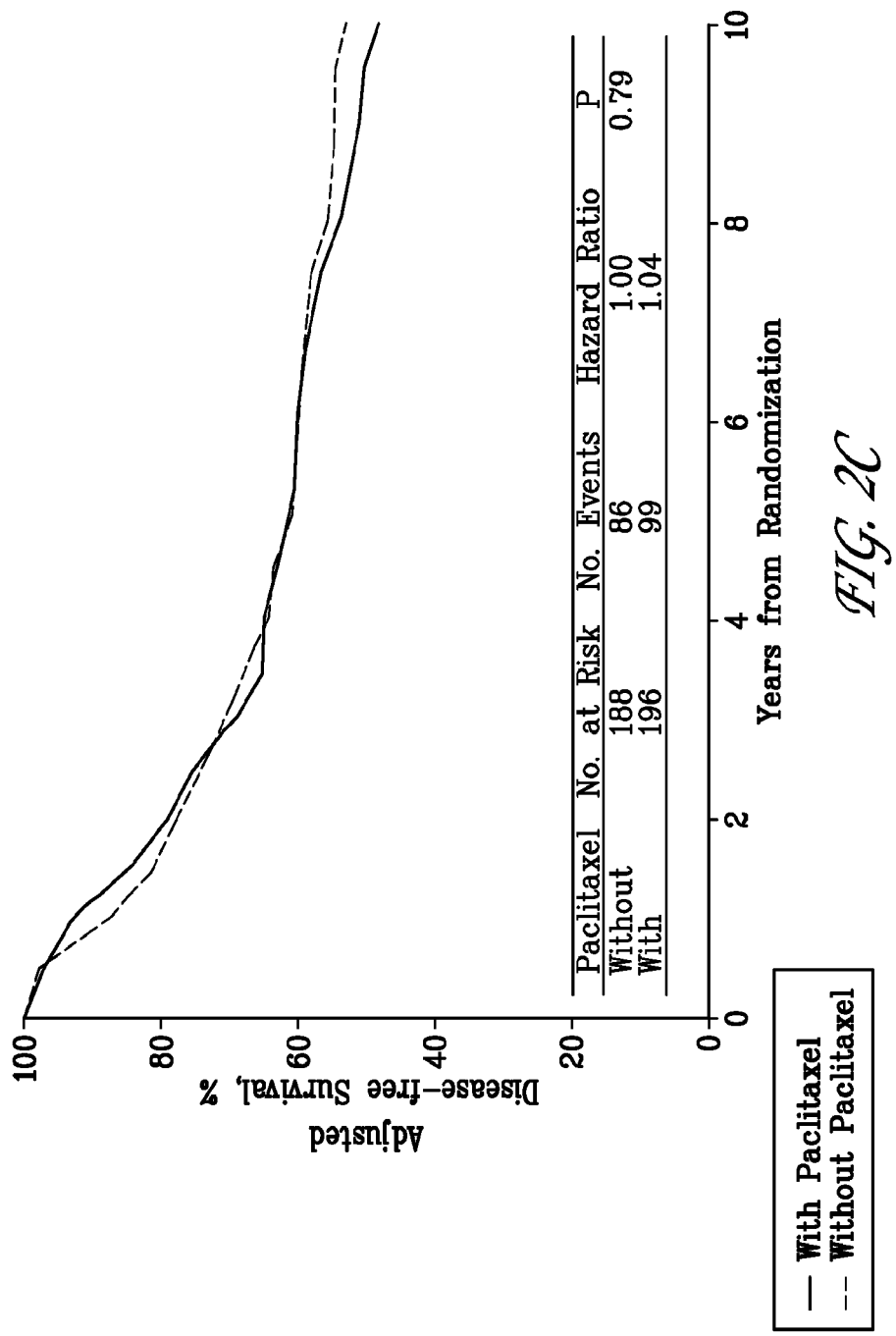
Figure 2D:
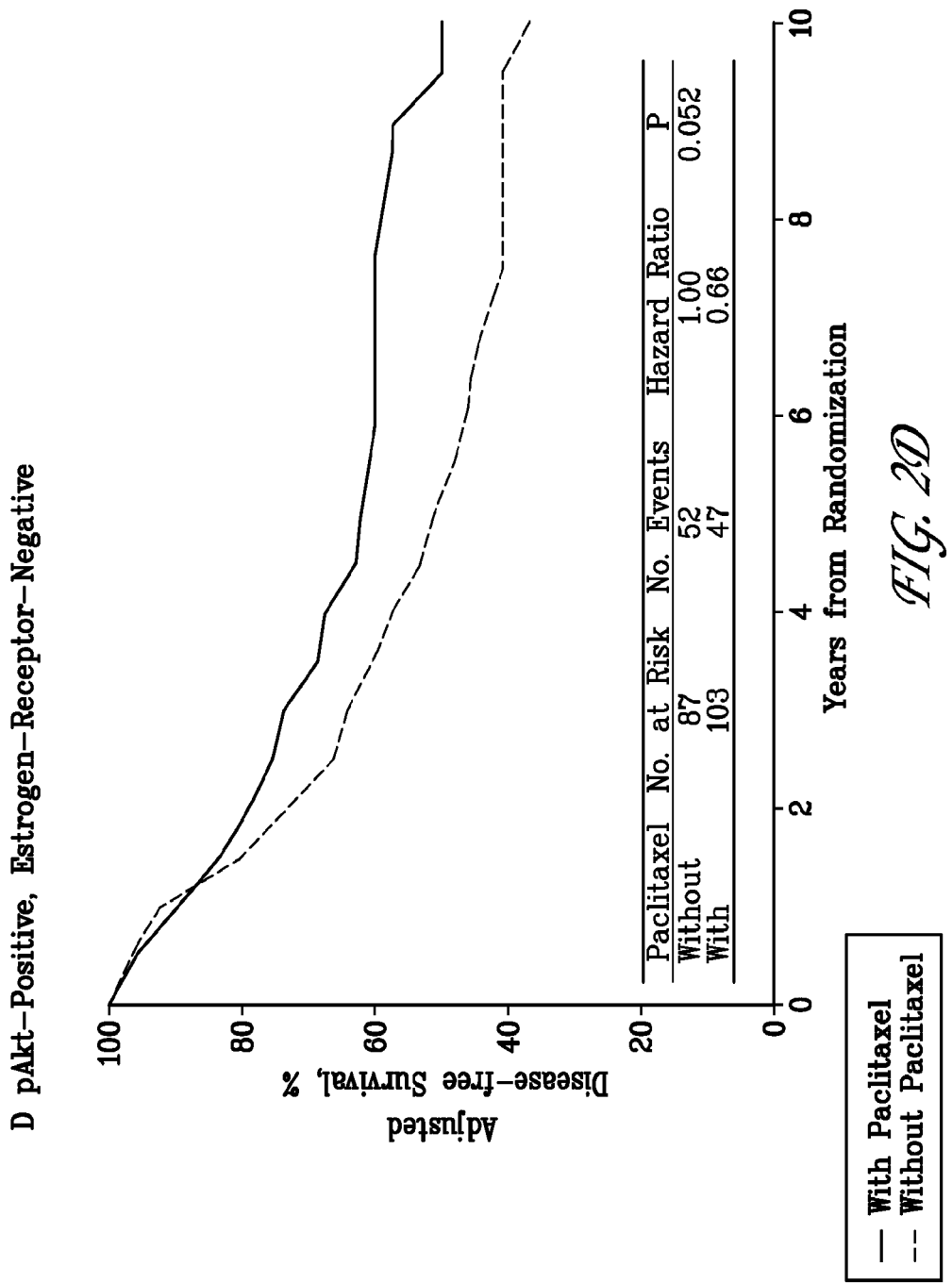
Figure 3A:
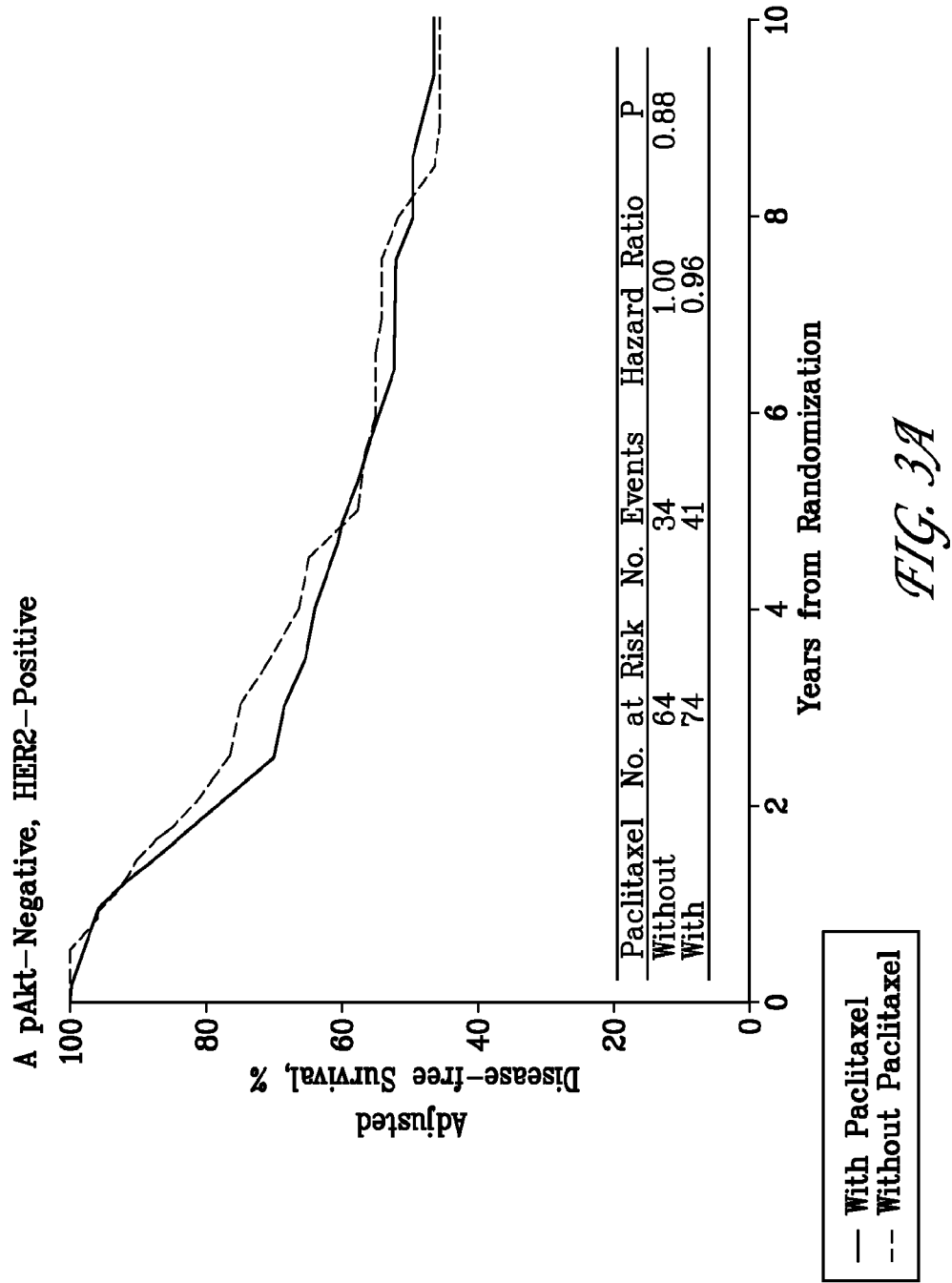
FIG. 3 (A-D) shows the adjusted disease-free survival curves stratified by HER2 status.
Figure 3B:
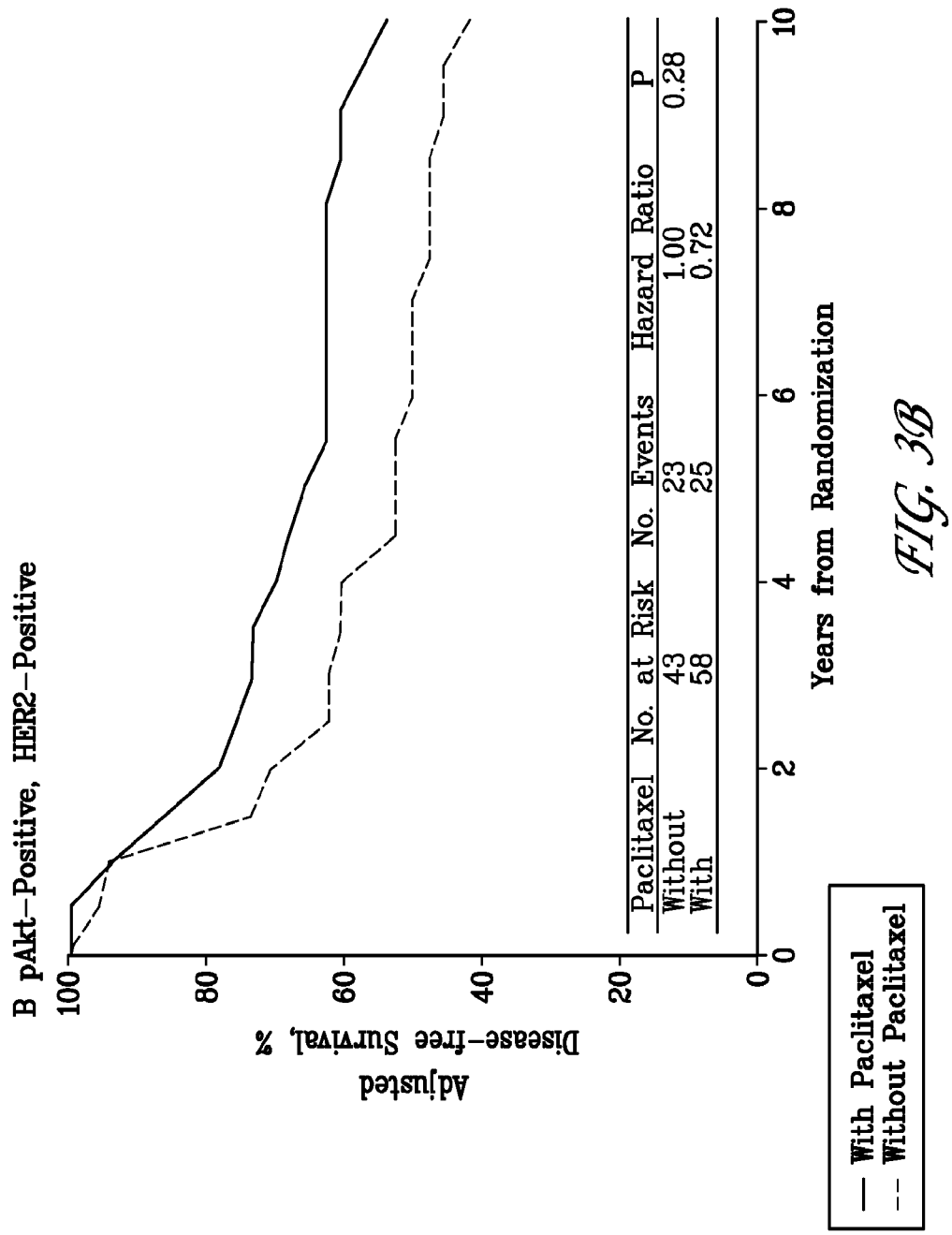
Figure 3C:
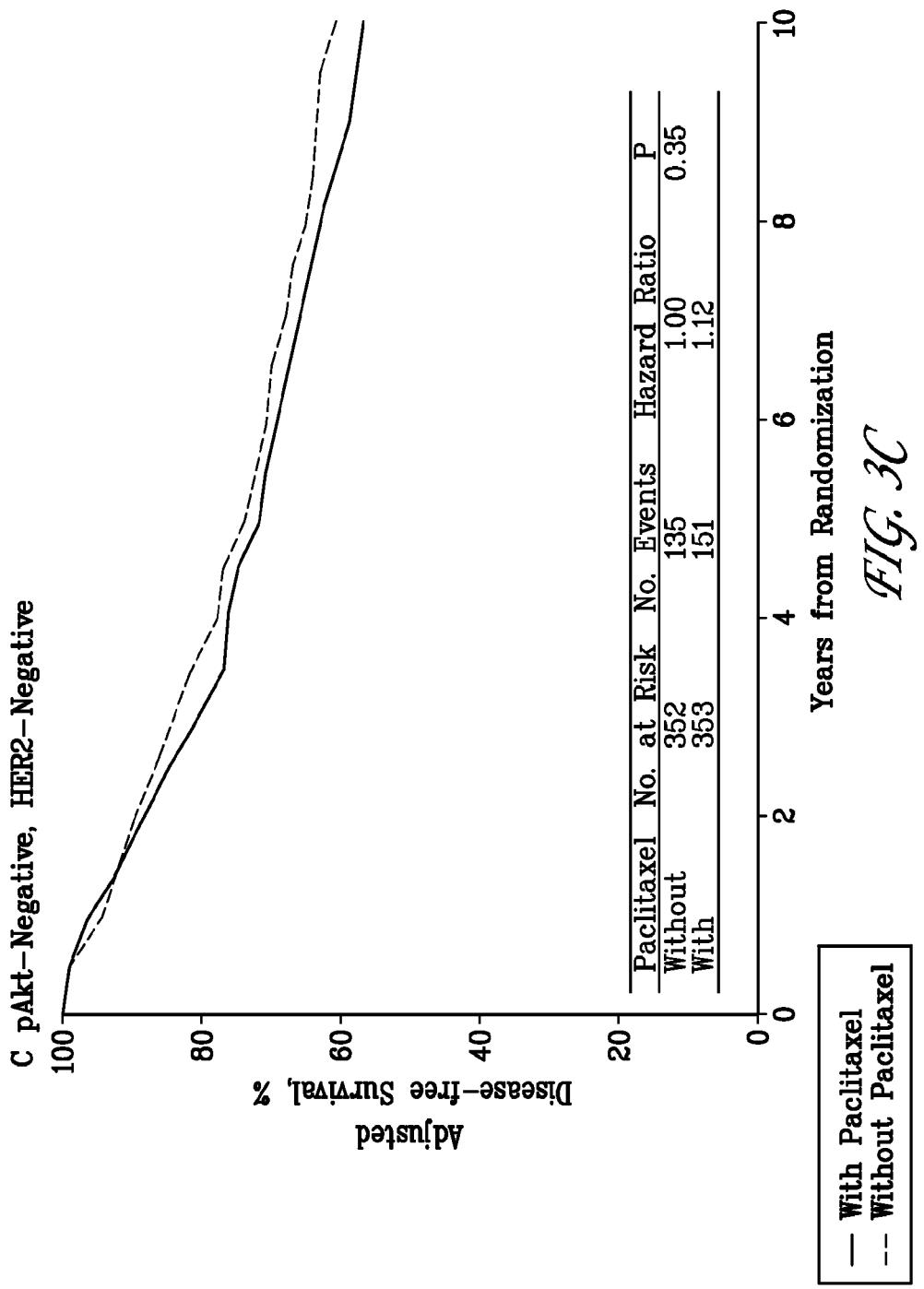
Figure 3D:
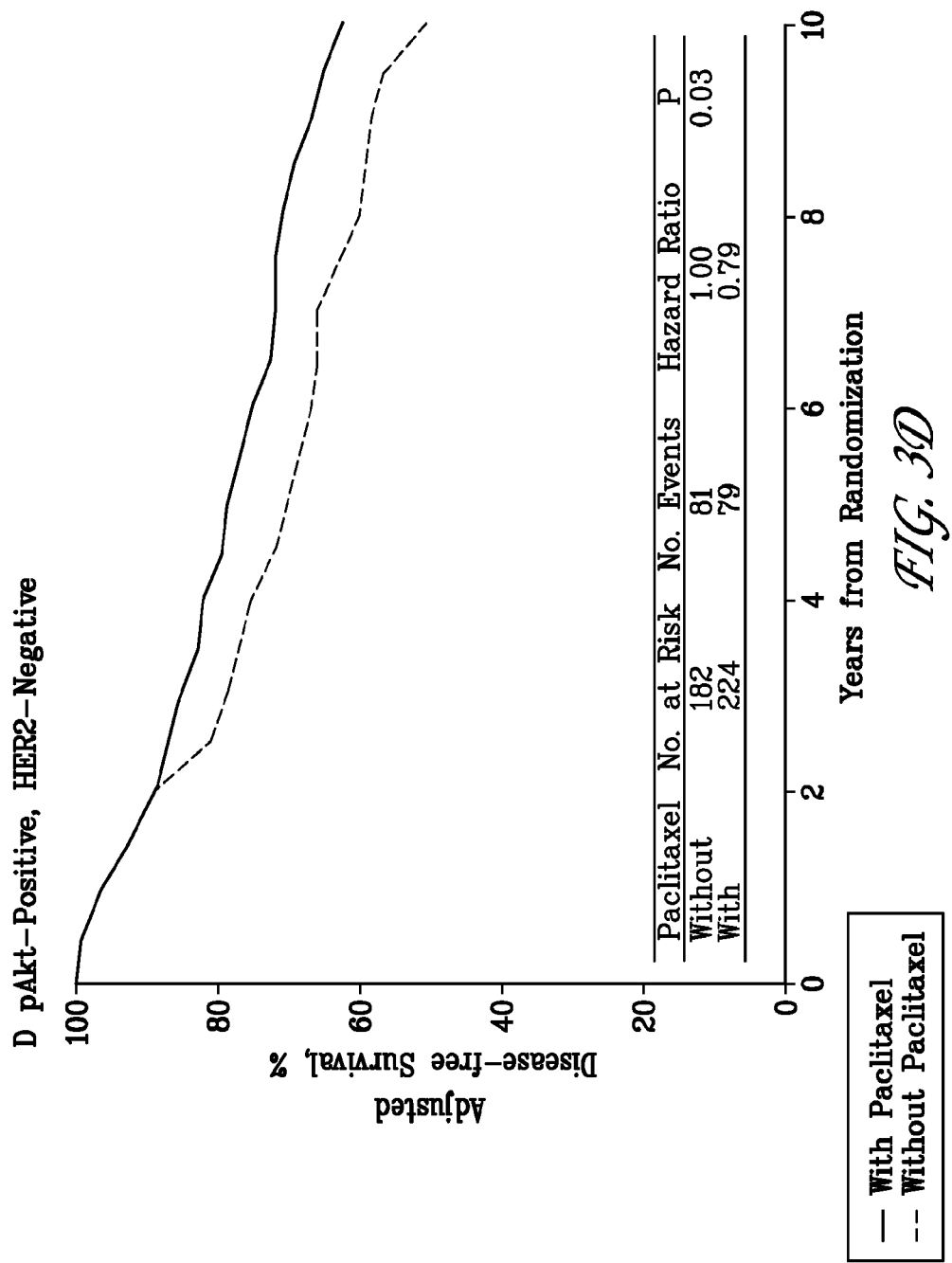

Paclitaxel and Akt-Ser473 Phosphorylation and Estrogen-Receptor Status or Her2 Status To explore the possible influence of estrogen-receptor and HER2 status on the response to the addition of paclitaxel chemotherapy in breast cancer, we performed exploratory analysis of disease-free survival for patient subgroups stratified by estrogen receptor status or HER2 status adjusting for age, tumor grade, tumor size, number of positive nodes, and either estrogen receptor or HER2 status. FIG. 2 provides the adjusted Kaplan-Meier plots for disease-free survival in patients with pAkt-negative and pAkt-positive cancer stratified by estrogen receptor status; FIG. 3 shows the adjusted disease-free survival curves stratified by HER2 status. In patients with pAkt-negative cancer, there was no suggestion of a paclitaxel effect among any of the estrogen-receptor status or HER2 status subgroups. The hazard ratios comparing the treatment groups were 1.06 for patients with estrogen-receptor positive tumors (P=0.64; FIG. 2A); 1.04 for estrogen-receptor-negative tumors (P=0.79; FIG. 2C); 0.96 for HER2-positive tumors (P=0.88; FIG. 3A); and 1.12 for HER2-negative tumors (P=0.36; FIG. 3C). By contrast, in patients with pAkt-positive cancer, the hazard ratios for the addition of paclitaxel compared with no-paclitaxel were 0.66 for those with estrogen receptor-negative tumors (P=0.052; FIG. 2D) and 0.70 for HER2-negative tumors (P=0.03; FIG. 3D). The plots for patients with estrogen receptor-positive (FIG. 2B) and with HER2-positive tumors (FIG. 3B) also showed separation between treatment curves but was not statistically significant. The hazard ratios comparing treatment groups were 0.82 for estrogen receptor-positive tumors (P=0.24) and 0.72 for HER2-positive tumors (P=0.28). These results indicate that the interaction between treatment and pAkt status are still evident after stratification with estrogen receptor status or HER2 status.

The foregoing results indicate that Akt-Ser473 phosphorylation predicts a significant benefit in disease-free survival in women with node-positive breast cancer who received additional four cycles of paclitaxel after four cycles of doxorubicin plus cyclophosphamide therapy. It seems that there is an interaction between pAkt and treatment with the addition of paclitaxel after adjuvant doxorubincin plus cyclophasphomide chemotherapy.

Reports from small data sets have studied the roles of Akt-Ser473 phosphorylation in hormonal therapy and prognosis using archived tissue samples. However, due to the concerns on variation in specimen fixation and duration of fixation for phospho-protein antigens, we optimized pAkt immunohistochemistry prior to this study. The determination of pAkt status by this optimized staining protocol facilitated the identification of benefiting patients. The use of clinically validated digital imaging assisted analyses has empowered the study results by increasing objectivity, reliability and reproducibility.

Recently, a meta-analysis showed a significant disease-free survival benefit from the taxane-based regimens in patients with both HER2-positive and HER2-negative cancers. More recently, a study in the adjuvant chemotherapy of breast cancer found that patients with HER2-negative breast cancer significantly benefit from weekly paclitaxel treatment (Sparano et al, 2008, NEJM). Therefore, patients are currently considered for adjuvant taxane-based chemotherapy regardless of either estrogen receptor status or HER2 status.

In this study, our results demonstrate that breast cancer patients with pAkt-positive cancer benefit from the addition of paclitaxel regardless of estrogen receptor status and HER2 status. By exploratory subset analyses, we found that there appears to have a greater benefit from paclitaxel in patients with pAkt-positive and ER-negative cancer than those with pAkt-positive and ER-positive cancer (FIG. 2B and FIG. 2D). The results are in agreement with meta-analysis data that ER-negative breast cancer benefits from the taxanes. In the subgroup of pAkt-positive and HER2-negative breast cancer, which represents a quarter of this study population, patients treated with paclitaxel compared with those not treated with paclitaxel did have a significantly increased disease-free survival (FIG. 3D). Also, the results from a small subset of patients with pAkt-positive and HER2-positive cancer suggested a benefit from paclitaxel (FIG. 3B).

Our results indicate that pAkt positive status independently predicts a disease-free benefit from the addition of paclitaxel after doxorubicin and cyclophasphomide chemotherapy. The results for the entire B-28 population with pAkt-Ser473 measurements (regardless of positive or negative status) demonstrated that the sequential addition of paclitaxel improved disease-free survival by 6% through approximate 10 years of follow-up. In the patient population with pAkt-positive breast cancer, however, the sequential addition of paclitaxel significantly improved disease-free survival by 26%.

Women with pAkt-negative tumors (62% in this study) did not appear to benefit from the addition of paclitaxel. Thus, the addition of paclitaxel to adjuvant chemotherapy regimen(s) could be spared for about two-Thirds of node-positive breast cancer patients if our data are validated in CALGB39344 or E1199 trial or other prospective clinical trials. pAkt as a predictive biomarker will then likely contribute to an approach of individualized medicine.

Women with pAkt-negative cancer which represent about 62% of node-positive breast cancer population who either received (31%) or did not receive the addition of paclitaxel did not benefit from the treatment. Our data suggest the possibility of not giving paclitaxel to the patient population with pAkt-negative node-positive breast cancer although the results may need to be validated in other prospective clinical trials.

Those skilled in the art will appreciate that numerous changes and modifications may be made to the preferred embodiments of the present invention, and that such changes and modifications may be made without departing from the spirit of the invention. It is, therefore, intended that the spirit and scope of the appended claims should not be limited to the description of the preferred embodiments contained herein, but that the appended claims cover all such equivalent variations as fall within the true spirit and scope of the invention.

What is claimed:

1. A method to identify a human having breast cancer who is likely to benefit from a treatment regimen that includes treatment with a taxane compound, the method comprising:

(a) conducting at least one immunohistochemistry assay of a tumor tissue sample so as to obtain physical data regarding the expression status of phosphorylated Akt-Ser473 (pAkt) protein in the sample; and (b) identifying the human as one who is likely to benefit from a treatment regimen that includes treatment with a therapeutically effective amount of a taxane compound if the physical data indicate that the expression status of pAkt-protein in the sample is positive.

2. The method according to claim 1 wherein the at least one immunohistochemistry assay of whether the subject's breast cancer is pAkt positive comprises incubating an antibody specific for pAkt with the tissue sample from said breast cancer and detecting the presence of bound pAkt-specific antibody.

3. The method according to claim 2 wherein said method further comprises performing digital imaging on the tissue sample from the human.

4. The method according to claim 2, wherein the antibody specifically binds to a phosphorylated peptide consisting of the Akt sequence SERRPHFPQF{pSerine473}YSA-NH2 (SEQ ID NO: 1).

5. The method according to claim 1 wherein said breast cancer is treated by administration of a therapeutically effective amount of the taxane.

6. The method according to claim 5 wherein said breast cancer is first treated by administration of therapeutically effective amounts of an anthracycline plus cyclophosphamide.

7. The method according to claim 1 wherein said determination is made without regard to the breast cancer's estrogen receptor status and HER2 status.

8. The method according to claim 5 wherein said taxane compound is paclitaxel.

9. A method of treating a breast cancer in a subject, comprising:
    (a) obtaining a determination of whether said breast cancer is phosphorylated Akt-Ser473 (pAkt) positive; and
    (b) upon a determination that said breast cancer is pAkt positive, indicating that the subject is likely to benefit from treatment with a taxane compound, treating the subject with a therapeutically effective amount of the taxane.

10. The method according to claim 9 wherein said determination comprises incubating an antibody specific for pAkt with a sample from said breast cancer and detecting the presence of bound pAkt-specific antibody.

11. The method according to claim 9, wherein the antibody specifically binds to a phosphorylated peptide consisting of the Akt sequence SERRPHFPQF{pSerine473}YSA-NH2 (SEQ ID NO: 1).

12. The method according to claim 9 further comprising treatment with therapeutically effective amounts of an anthracycline and cyclophosphamide.

13. The method according to claim 9, wherein said taxane compound is paclitaxel.

14. A method of treating breast cancer in a patient, the method comprising:
    a) administering a therapeutically effective amount of a taxane compound after chemotherapy with therapeutically effective amounts of an anthracycline and cyclophosphamide, wherein a breast tumor tissue test sample is obtained from the patient, the expression status of phosphorylated Akt-Ser473 (pAkt) protein in the test sample is determined by a laboratory assay, and the pAkt protein in the test sample is expressed.

15. The method according to claim 14 wherein said laboratory assay comprises incubating an antibody specific for pAkt with a sample from said breast tumor tissue and detecting the presence of bound pAkt-specific antibody.

16. The method according to claim 15, wherein the antibody specifically binds to a phosphorylated peptide consisting of the Akt sequence SERRPHFPQF{pSerine473}YSA-NH2 (SEQ ID NO: 1).

17. The method according to claim 14, wherein said treatment with the taxane compound is provided as adjuvant chemotherapy.

18. The method of claim 14, where in the anthracycline is doxorubicin.

* * * * *

UNITED STATES PATENT AND TRADEMARK OFFICE
CERTIFICATE OF CORRECTION

PATENT NO. : 8,546,091 B2  Page 1 of 1
APPLICATION NO. : 13/322140
DATED : October 1, 2013
INVENTOR(S) : Yang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 63 days.

Signed and Sealed this

Fifteenth Day of September, 2015

Michelle K. Lee
*Director of the United States Patent and Trademark Office*